United States Patent [19]

Ohkuma et al.

[11] Patent Number: 5,380,717
[45] Date of Patent: Jan. 10, 1995

[54] FOOD COMPOSITE FOR PERFORMING FUNCTION OF LARGE BOWEL REGULATION

[75] Inventors: Kazuhiro Ohkuma; Shigeru Wakabayashi, both of Sanda; Mitsuko Satouchi, Takarazuka, all of Japan

[73] Assignee: Matsutani Chemical Industries Co., Ltd., Hyogo, Japan

[21] Appl. No.: 107,176

[22] Filed: Aug. 17, 1993

Related U.S. Application Data

[63] Continuation of Ser. No. 902,501, Jun. 23, 1992, abandoned, which is a continuation of Ser. No. 656,891, Feb. 19, 1991, abandoned.

[30] Foreign Application Priority Data

Feb. 22, 1990 [JP]  Japan ................... 2-41620

[51] Int. Cl.$^6$ ............. A61K 33/10; A61K 31/70; A61K 31/715; A23G 3/00
[52] U.S. Cl. .................... 514/58; 514/892; 424/439; 424/442; 426/658
[58] Field of Search ............ 426/658; 424/439, 442; 514/58, 892; 536/103

[56] References Cited

U.S. PATENT DOCUMENTS

| | | | |
|---|---|---|---|
| 2,494,191 | 1/1950 | Neumann | 536/102 |
| 3,086,008 | 4/1963 | Opila et al. | 536/103 |
| 3,974,032 | 8/1976 | Harjes et al. | 426/661 |
| 4,219,580 | 8/1980 | Torres | 426/549 |
| 4,247,568 | 1/1981 | Carrington et al. | 426/661 |
| 4,510,166 | 4/1985 | Lenchin et al. | 536/103 |

FOREIGN PATENT DOCUMENTS

| | | |
|---|---|---|
| 0368451 | 5/1990 | European Pat. Off. |
| 2-145169 | 6/1990 | Japan |
| 2-154664 | 6/1990 | Japan |
| 2-276556 | 11/1990 | Japan |

OTHER PUBLICATIONS

Patent Abstracts of Japan, vol. 11, No. 300, (C-449) [2747], 29th Sep. 1987; & JP-A-62-91501 (Sanmatsu Kogyo K.K. 27-04-1987.

"Grant and Hackh's Chemical Dictionary", Fifth Edition, 1987 p. 484.

Chemical Abstracts, vol. 84, No. 20, May 17, 1976, p. 118, Abstract No. 137552k.

Chemical Abstracts, vol. 109, No. 11, Sep. 12, 1988, p. 99, Abstract No. 95048c.

Patent Abstracts of Japan, vol. 8, No. 77 (C-218)(1514), Apr. 10, 1984.

Lehrbuch der Lebensmittelchemie, Josef Schormüller, 1974, p. 580.

Kohlenhydratreiche Lebensmittel, L. Acker, 1967, pp. 639–641.

Römpps Chemie-Lexikon, Dr. Otto-Albert Neumüller, 1981, p. 919.

Arzneimittel-wirkungen, Dr. Ernst Mutschler, p. 504, 1986.

Primary Examiner—Ronald W. Griffin
Attorney, Agent, or Firm—Sughrue, Mion, Zinn, Macpeak & Seas

[57] ABSTRACT

A food composite performing a function of large bowel regulation and comprising a refined product of pyrodextrin obtained as an active ingredient through a process of decomposing starch or starch hydrolyzate by heating in the presence of an acid or without acid.

11 Claims, No Drawings

FOOD COMPOSITE FOR PERFORMING FUNCTION OF LARGE BOWEL REGULATION

This is a continuation of application Ser. No. 07/902,501 filed Jun. 23, 1992, which is a continuation of application Ser. No. 07/656,891, filed on Feb. 19, 1991, both now abandoned.

BACKGROUND OF THE INVENTION

1. Field of the Invention

The present invention relates to a food composite capable of performing a function of large bowel regulation and improvement in constipation.

2. Description of Prior Art

Hitherto, food fibers, food stuffs containing bifido bacterium, and oligosaccharides performing an action of multiplying bifido bacterium have been suggested as food materials effective for intestinal adjustment and improvement in constipation. Generally, dietary fibers are divided into water-soluble dietary fibers and insoluble ones, and their typical physiological functions have been reported as follows:

(1) function of reducing cholesterol in serum and liver;

(2) function of saving the increase of blood glucose; and (3) function of regulating large bowel.

Among those functions, the large bowel regulation is generally said effective for preventing intestinal disorders by the improvement of intestinal flora, the acceleration of large bowel persitalsis through water absorption as well as volume effect, the normalization of internal pressure of large intestines, the increase of feces amount, the dilution of harmful objects, and the inhibition of harmful object. It is also said that the insoluble fibers represented by cellulose perform not only desirable physiological functions such as inhibition from increase of blood glucose, restraint of absorption of cholesterol, but also undesirable function of inhibiting absorption of useful metals because of high viscosity. Moreover, such high viscosity pertinent to the insoluble dietary fibers make it difficult to be taken in in a large amount, thus uses of the insoluble dietary fibers being quite limited.

On the other hand, it is said that oligosachhadrides having an action of multiplying bifido bacterium are not absorbed in the alimentary canal, but, reaching the colon, they are conduced by intestinal bacteria, in particular, bifido bacterium; that acid produced as a result of such conduciveness stimulates intestinal walls; and that difference in conduciveness of other bacterias brings change in intestinal florae, all of the foregoing actions eventually resulting in intestinal adjustment.

In this respect, it is to be noted that the intestinal flora vary widely due to ages and eating habits of individual persons. Furthermore, there are various conduciveness depending upon the kinds of oligosaccharides. For example, it is certain that some of them performs a function of multiplying bifido bacterium, but they also performs a function of multiplying other harmful bacteria, thus there being no absolute superiority among them.

Moreover, oligosaccharides are often used as sweetening agent, and since they are of low molecular substance not to be absorbed in the alimentary canal and go down to the colon, they sometimes result in diarrhea.

The inventors of the present application have already noticed the existence of indigestible substance contained in pyrodextrin that has never been considered as food material and developed a method for preparing indigestible dextrin to be used as a food material from the mentioned pyrodextrin. Furthermore, the inventors have examined and seeked for physiological functions of indigestible dextrin as a dietary fiber, and have come up with a novel idea of further developing a food composite performing a function of large bowel regulation from the indigestible dextrin.

Dietary fibers are usually defined as "the whole of indigestible ingredients that are contained in foodstuff and are not digested by man's digestive enzymes" or "the indigestible high polymer compounds that are contained in foodstaff and have physiological activities". In this sense, it may be said that the indigestible dextrin is one of dietary fibers.

SUMMARY OF THE INVENTION

Accordingly, an object of the present invention is to materialize a new idea as mentioned above, in other words, to develop a new food composite from pyrodextrin a new food composite capable of performing a function of large bowel regulation on the basis of the mentioned new concept.

The foregoing object of the invention is accomplished by employing pyrodextrin that can be obtained through a process wherein starch or starch hydrolyzate is decomposed by heating in the presence of an acid or without an acid, and a refined product of the mentioned pyrodextrin serving as a main composition of food composites performing a function of large bowel regulation.

As mentioned above, the invention is based on a novel concept that the refined pyrodextrin obtained through the process of decomposing at least one of starch or starch hydrolyzate by heating with or without acid performs an extremely effective function of large bowel regulation.

Described hereunder is a process for preparing pyrodextrin in accordance with the invention.

As for a raw starch, that is, a starch to be employed in embodying the invention, a wide range of starches such as potato, corn, and cassaba can be utilized. It is also preferable to employ those starches in the form of processed food commercially available in the market. In this case, enumerated as processed starches are, for example, soluble starch, esterified starch, etherified starch, cross-linked starch and, preferably, starch phosphate and hydroxypropyl starch.

Furthermore, as a material employed in embodying the invention, starch hydrolyzate is used other than the starches mentioned above. This starch hydrolyzate is obtained by slightly hydrolyzing a starch, and in such hydrolyzation, an acid or an enzyme may be added. The hydrolyzation degree of starch should be in the range of DE3 to DE40, and the added acid should be a normally oxalic acid or a hydrochloric acid with their amount in the range of 0.01% to 0.1% (in terms of the weight of starch). In addition, α-amylase can be used as an enzyme.

These raw materials in accordance with the invention are decomposed by heating, preferably, under normal pressure. The decomposition by heating is achieved by heating the materials at a temperature from about 150° C. to 220° C. for 1 to 5 hours. The pressure at the heating may be the normal one without necessity of either under vacuum or pressure. At this heating step, it is also preferable to add an acid as a catalyst for heating decomposition. As the acid to be adopted as the catalyst, mineral acids such as sulfuric acid, hydrochloric acid and nitric acid can be used, and in particular, hydrochloric acid is preferable when added in an amount of several % by weight to the materials to have a concentration of 1% by weight. The acid should be added evenly, being, preferably, well mixed by spraying. The mixture is then preferably dried up preliminarily at a temperature from about 100° C. to 120° C. so as to reduce the moisture to about 5%.

The dextrin in accordance with the invention obtained in the mentioned process, that is, pyrodextrin is then subject to refining. The refining process is now described hereunder:

At least one treatment of following (a) and (b) are employed:
  (a) After a hydrolysis with α-amylase, or after a hydrolysis with glucoamylase following the hydrolysis with α-amylase, the solution is refined through known processes of filtration, decolorization, and deionization.
  (b) After completing of the treatment (a), a further treatment separates dextrin fraction with chromatography by ion-exchange resins.

Further description on the treatments (a) and (b) is given in detail as follows:

In the treatment (a), pyrodextrins are dissolved in water to obtain a solution of 30% to 50% by weight, and then neutralized to pH5.5 to 6.5, preferably to pH5.8, and 0.05% to 0.2% by weight of α-amylase (available in the market, either one originated from mold or the one from bacteria may be applied) based on the pyrodextrin is added to the solution, and then at the reaction temperature of said amylase in the range from about 85° C. to 100° C., the solution is hold for 30 minutes to 2 hours. Subsequently, the temperature of the solution is raised up to 120° C. to complete the reaction of α-amylase. Thereafter, the temperature of the solution is decreased to about 55° C., and the solution is adjusted to about pH5.5, then 0.05% to 0.2% by weight of glucoamylase (popularly used) based on the original pyrodextrin is added. The solution is kept at a temperature to allow its action for 24 to 48 hours. This action aims at decomposition of small molecules such as oligosaccharides into glucose. Following this step, temperature of the solution is raised up to, for example, about 80° C. to complete the reaction of glucoamylase.

On the other hand, in the treatment (b), chromatographic separation by ion-exchange resin is conducted. In this treatment, strongly acidic ion-exchange resins sold widely on the market can be employed.

Preferable as concrete examples are Amberlite IR-116, IR-118, IR-120B, XT-1022E, XT-471F (all manufactured by Organo), Diaion SK-1B, SK-102, SK-104, SK-106, SK-110, SK-112, SK-116, FR-01 (all manufactured by Mitsubishi Chemicals), and XFS-43281.00, XFS-43280.00, XFS-43279.00, XFS-43278.00 (all manufactured by Dow Chemicals).

These resins are preferably dealt with as alkaline metal type or alkaline earth metal type before their uses. It is preferable to adjust the rate of flow at the time of a column fluid according to a resin to be used. The rate of flow of the fluid is preferably in the range of SV=0.1 to 0.6. The rate of flow out of the above range is tend to deteriorate the workability and separation. The temperature at the time of running the fluid is preferably in the range from 20° C. to 70° C., and a temperature below this range will deteriorate the separation and make the viscosity of fluid get high, thereby giving a negative influence on the fluid, while a temperature exceeding this range will cause the fluid to be tanned and deteriorate other quality characteristics.

When observing carefully the dextrin refined from the mentioned pyrodextrin, it was recognized that their linkages were not only 1→4 and 1→6 bonds with glucose as structural sugar, but also 1→2 and 1→3 bonds. Further, a part of reducing end group is of 1-6-anhydroglucose.

Viscosity of this pyrodextrin is rather low, i.e., about 10 cps (30%, 30° C.), and it tastes slightly sweet and is orderless, with the number of 1→2 and 1→3 bonds below about 10%. The pyrodextrin is, therefore, easily employed as a material for various beverages and processed foods and, furtherfore, it is as safe to be eaten as maltodexitrin since its raw material is starch.

The most advantageous characteristics of the present invention exists in that the dextrin performs a function of large bowel regulation and can be employed as a food material exhibiting such an large bowel regulating function.

The term "function of intestinal regulation" used herein means a function of preventing various large intestinal disorders by the improvement of intestinal flora, the acceleration of large bowel persitalsis through water absorption as well as volume effect, the normalization of internal pressure of large intestine, the increase of feces amount, the dilution of harmful objects, and the inhibition of harmful object.

In this manner, the pyrodextrin serving as the above food material in accordance with the invention can be widely used as a material for various foods, and its uses extend to any food so far as it is used as a material for food. Typical foods in this sense are, for example, beverages, desserts and candies.

Other objects, features and advantages of the invention will become apparent in the course of the following description.

DESCRIPTION OF THE PREFERRED EMBODIMENTS

Several examples in accordance with the present invention is hereinafter described in more detail in comparison with referential examples of process for preparing pyrodextrin.

REFERENTIAL EXAMPLE 1

5000 Kgs of potato starch commercially available in the market were put into a Ribbon-Mixer, 150 liters of 1% hydrochloric acid were then sprayed, stirred and uniformized with a mixer, and further allowed to mature in the Ribbon-Mixer for 5 hours. This mixture was preliminarily dried up to be 3% of moisture, subsequently put into a Rotary-Kiln type converter successively to be heated at a temperature of 180° C. for 2 hours.

Then, 4000 liters of water was added to 2000 kgs of pyrodextrin obtained through the above process, and after being adjusted to pH6.0, 0.2% of α-amylase ("Termamyl 60L" produced by Novo) was added to such solution of pyrodextrin, which is further allowed to be hydrolyzed at a temperature of 95° C. for 1 hour. After completing such reaction, the solution was refined through the process of decolorization, deionization and so on, then finally dried by means of a spray dryer to obtain approximately 1700 kgs of powder. Properties of the dextrin thus obtained were as follows:

| | |
|---|---|
| DE = 10 | |
| Type of bonds | |
| Terminal | 24% |
| 1 → 4 | 58% |
| 1 → 6 | 12.3% |
| 1 → 2, 1 → 3 | 5.7% |
| Indigestible portion | 58% |

EXAMPLE 1

A dosage test of 35 gs of the dextrin obtained in the above Referential example 1 was conducted on five healthy adult men over a test term of two weeks. The contents of meals during both first and second weeks of the test term were prepared to be the same. A dosage of 35 gs of the dextrin was given to them after breakfast from Monday to Friday respectively, then their feces were collected to measure and record wet weight of the feces, dry weight of the feces, water amount of the feces, percentage of moisture content in the feces, and frequency of evacuation. As a result of this, following data were obtained and they proved explicitly that the dosage performed a function of increasing total amount of feces.

TABLE 1

| Test term | No intake term | Intake term |
|---|---|---|
| Wet weight of feces | 565 ± 58 | 770 + 92* |
| Dry weight of feces | 121 ± 4.9 | 158 ± 11* |
| Water amount of feces | 445 ± 54 | 612 ± 84* |
| Percentage of moisture content in feces | 77.0 ± 1.7 | 77.6 ± 1.8 |
| Frequency of evacuation | 4.7 ± 0.4 | 5.9 ± 0.4* |

Note that shown in the above TABLE 1 are the average values of the measured values ± standard error.
The mark * shown that there is a significant difference of 5% of peril rate with respect to the "no intake term".

EXAMPLE 2

An examination was executed to confirm the effect of relieving constipation performed by the dextrin obtained in the above Referential example 1. A certain amount of the dextrin was given to 30 volunteers who were apt to be constipated for not less than 5 days, and then the difference of feces between the times before and after the dosage was investigated in the form of a questionnaire. Items of the questionnaire were scored and then statistical processing of the data thus obtained was conducted with regard to the times before and after the dosage to recognize the effect of relieving constipation. The results have revealed that a dosage not less than 5 gs exhibited the effect of relieving constipation.

| | Number of points |
|---|---|
| Frequency of evacuation | |
| once or more per day | 4 |
| once per day | 3 |
| once per two days | 2 |
| once per three days and irregularly | 1 |
| Amount of feces | |
| much | 4 |
| nomal | 3 |
| little | 2 |
| a little, or none | 1 |
| Condition of feces | |
| laxative | 4 |
| soft | 3 |

-continued

| | Number of points |
|---|---|
| normal | 2 |
| hard | 1 |
| Feeling after evacuation | |
| felt refreshed | 4 |
| felt soft faces left, normal | 3 |
| felt laxative feces left | 2 |
| felt hard feces left | 1 |

TABLE 2

| | Group of 5 g Dosage N = 13 (including 3 men) | Group of 10 g Dosage N = 17 (including 4 men) |
|---|---|---|
| Before dosage | 8.56 ± 1.9 | 10.40 ± 1.4* |
| After dosage | 7.50 ± 1.4 | 11.60 ± 2.1** |

The mark * shows a significant difference by 2% of peril rate. The mark ** shows a significant difference by 0.2% of peril rate.

REFERENTIAL EXAMPLE 2

50 kgs of pyrodextrin (Arabix #7 produced by Matsutani Chemicals) was dissolved in 100 kgs of water, adjusted to pH5.5, and 0.2 weight % of α-amylase (Klaistase KD produced by Daiwa Kasei Co.) was added, and allowed to react at 85° C. for one hour. Then the solution was kept at a temperature of 120° C. for 15 minutes to terminate the reaction of α-amylase, and decreasing the tempreture down to 55° C., adjusted to pH4.5, and 0.1 weight % of glucoamylase (produced by Daiwa Kasei) was added and saccharified for 36 hours. At this step, the solution was adjusted to pH3.5 to terminate the reaction of glucoamylase. Subsequently, the solution was refined through activated chacoal and ion-exchange resin and then concentrated to obtain 75 kg of a 50% solution. This solution was caused to pass through five columns filled up with an alkaline metal type strongly acidic ion-exchange resin, XFS-432795L at SV=0.25 to extract high molecular weight indigestible dextrin. Its average molecule weight was 1600, its indigestible portion was 92%, type of bonds terminal 24%, 1→4 58%, 1→4 12.3%, 1→2, 1→3 5.7%, respectively.

EXAMPLE 3

Six Wister-desent male rats were put in separate cages disposed in a room of a temperature 23° C.±2° C. and raised for several days preliminarily, then given basal feed, a mixture of basal feed and 7.5% of the dextrin obtained in the referential example 2, and a mixture of basal feed and 7.5% of cellulose (Solkaflock produced by Sanyo Koukoku Pulp Co.) with water. The rats were allowed to have them for seven days. The amount of their intakes and their weight were measured and recorded every day. In the morning of the 7th day, their blood were collected from heart to be killed under anethesia, and their cecums were extracted in order to measure the weight thereof as well as pH and content of volatile acid in the contents within the cecums. The results were as follows:

TABLE 3

| | Weight of cecum | pH of contents | Volatile acid (As acetic acid/ cecum) |
|---|---|---|---|
| Basal feed | 1.2 g ± 0.2 | 7.6 ± 0.1 | 19 mg ± 4 |

TABLE 3-continued

|  | Weight of cecum | pH of contents | Volatile acid (As acetic acid/cecum) |
|---|---|---|---|
| Basal feed and dexrin | 3.8 g ± 0.2 | 5.9 ± 0.2 | 81 mg ± 7 |
| Basal feed and cellulose | 1.5 g ± 0.4 | 7.5 ± 0.2 | 19 mg ± 3 |

It was acknowledged from the above table 3 that the dextrin obtained in the referential example reached the cecum without sufficient digestion, and caused organic acid fermentation within large intestine, thereby significantly reducing pH in the large intestine.

REFERENTIAL EXAMPLE 3

5 kgs of starch hydrolyzate of DE3 (Pinedex No. 100 (produced by Matsutani Chemicals) was dissolved in 15 liters of water, 250 ppm (based on the starch hydrolyzate) of hydrochloric acid was added, then spray-dried to obtain 4.5 kg or powder. Subsequently, the powder was put in an oil bath to be heated at a temperature of 180° C. for one hour in dry process. Then the powder was dissolved in water, adjusted to pH6.0 with sodium hydroxide, and spray-dried. The DE of the dextrin obtained through this process was 7.2, its average molecular weight was 2500, its indigestible portion was 61%, respectivey.

EXAMPLE 4 TO 7

With the dextrin obtained in the Referential Example 3, carbonated soda (Example 4), ice milk (Example 5), Jelly (Example 6), and Bavarian cream (Example 7) were produced by a known method under the prescriptions shown below, respectively:

| Prescription for carbonated soda | |
|---|---|
| Dextrin of referential example 3 | 50 g |
| Granulated sugar | 125 g |
| Citric acid | 1.5 g |
| Sodium citrate | 0.1 g |
| Vitamin C | 0.15 g |
| Soda-pop essence | 1 g |
| Carbonated water | 520 g |
| Water | 385 g |
| Prescription for ice milk | |
| Nonfat powdered milk | 54.0 g |
| Sweetened all fat condensed milk | 176.4 g |
| Sweetened non fat condensed milk | 122.4 g |
| Salt-free butter | 30.0 g |
| Water | 700.6 g |
| Vegetable oil and fat | 36.0 g |
| Sugar | 18.0 g |
| Corn Syrup | 30.0 g |
| Dextrin of referential example 3 | 24.0 g |
| Emulsifier | 6.2 g |
| B-carotene | 0.24 g |
| Flavor | 1.8 g |
| Prescription for jelly | |
| (in case using agar) | |
| Agar | 4 g |
| Water | 350 g |
| Sugar | 60 g |
| Fruit juice | 150 g |
| Dextrin of Referential example 3 | 10 g |
| (in case using gelatin) | |
| Gelatin | 10 g |
| Water | 280 g |
| Sugar | 60 g |
| Fruit juice | 150 g |
| Dextrin of referential example 3 | 10 g |

| -continued | |
|---|---|
| Prescription for Bavarian Cream | |
| Milk | 140 g |
| Raw cream | 57 g |
| Egg yolk | 20 g |
| Gelatin | 9 g |
| Sugar | 38 g |
| Water | 36 g |
| Dextrin of referential example 3 | 30 g |

The invention may be embodied in other specific forms without departing from the spirit or essential characteristics thereof. The foregoing examples are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method for regulating large bowel function which comprises the steps of:
   (a) providing an indigestible dextrin which is obtained by heating starch in the presence of a mineral acid to prepare pyrodextrin, hydrolyzing the pyrodextrin with α-amylase and refining the hydrolyzed pyrodextrin; and
   (b) administering an effective amount of the indigestible dextrin to an animal.

2. The method of claim 1, wherein said indigestible dextrin contains 1→4, 1→6, 1→2 and 1→3 linkages and a part of reducing terminal groups of said indigestible dextrin are 1→6 anhydroglucose.

3. The method of claim 1, wherein said indigestible dextrin is obtained by heating said starch in the presence of hydrochloric acid in an amount of 0.01 to 0.1% by weight based on the weight of said starch at 150° C. to 220° C. for 1 to 5 hours to prepare pyrodextrin, dissolving the pyrodextrin in water in an amount of 30 to 50% by weight based on the weight of the solution, adjusting the pH of the solution to pH 5.5 to 6.5, treating the solution with α-amylase in an amount of 0.05 to 0.2% by weight based on the weight of the pyrodextrin at 85° C. to 100° C. for 0.5 to 2 hours, and refining the hydrolyzed pyrodextrin.

4. The method of claim 1, wherein said animal is human being and said indigestible dextrin is administered to the human being in an amount of 5 to 35 g per day.

5. The method of claim 4, wherein said indigestible dextrin is administered in the form of food containing the same.

6. A method for regulating large bowel function which comprises the steps of:
   (a) providing an indigestible dextrin which is obtained by heating starch in the presence of a mineral acid to prepare pyrodextrin, hydrolyzing the pyrodextrin with α-amylase and then with glucoamylase, and subjecting the hydrolyzed dextrin to ion exchange resin chromatography to refine the hydrolyzed pyrodextrin; and
   (b) administering an effective amount of the indigestible dextrin to an animal.

7. The method of claim 6, wherein said indigestible dextrin contains 1→4, 1→6, 1→2 and 1→3 linkages and a part of reducing terminal groups of said dextrin are 1→6 anhydroglucose.

8. The method of claim 6, wherein said indigestible dextrin is obtained by heating said starch in the presence of hydrochloric acid in an amount of 0.01 to 0.1% by weight based on the weight of said starch at 150° C. to 220° C. for 1 to 5 hours to prepare pyrodextrin, dissolving the pyrodextrin in water in an amount of 30 to 50% by weight based on the weight of the solution, adjusting the pH of the solution to pH 5.5 to 6.5, treating the solution with α-amylase in an amount of 0.05 to 0.2% by weight based on the weight of the pyrodextrin at 85° C. to 100° C. for 0.5 to 2 hours, treating the solution with glucoamylase in an amount of 0.05 to 0.2% by weight based on the weight of the pyrodextrin at about 55° C. for 24 to 48 hours, refining the hydrolyzed pyrodextrin and subjecting the hydrolyzed and refined pyrodextrin to ion exchange resin chromatography to separate a high molecular weight indigestible dextrin fraction.

9. The method of claim 8, wherein said ion exchange resin is an alkaline metal or alkaline earth metal type of strongly acidic ion exchange resin.

10. The method of claim 6, wherein said animal is human being and said indigestible dextrin is administered to the human being in an amount of 5 to 35 g per day.

11. The method of claim 10, wherein said indigestible dextrin is administered in the form of food containing the same.

* * * * *